(12) United States Patent
Auer et al.

(10) Patent No.: US 6,696,603 B2
(45) Date of Patent: Feb. 24, 2004

(54) METHOD FOR CLEANING OFF-GAS FLOWS

(75) Inventors: Heinz Auer, Neulussheim (DE); Bernd Bessling, Grosse Ille, MI (US); Hans Hammer, Mannheim (DE); Hans Hasse, Kaiserslautern (DE); Friedrich Sauer, Obersülzen (DE); Maximilian Vicari, Limburgerhof (DE); Gerhard Wagner, Ludwigshafen (DE); Till Adrian, Bobenheim-Roxheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/181,458
(22) PCT Filed: Jan. 24, 2001
(86) PCT No.: PCT/EP01/00747
§ 371 (c)(1), (2), (4) Date: Jul. 18, 2002
(87) PCT Pub. No.: WO01/55070
PCT Pub. Date: Aug. 2, 2001

(65) Prior Publication Data
US 2003/0050506 A1 Mar. 13, 2003

(30) Foreign Application Priority Data
Jan. 24, 2000 (DE) .................................. 100 02 790

(51) Int. Cl.$^7$ .............................................. C07C 53/02
(52) U.S. Cl. ................................................. 562/609
(58) Field of Search ...................................... 562/609

(56) References Cited

U.S. PATENT DOCUMENTS
4,326,073 A * 4/1982 Wolf et al. .................. 562/609

FOREIGN PATENT DOCUMENTS
EP 017 866 10/1980

OTHER PUBLICATIONS
Ullmanns Enc., Band 7, pp. 365–366.
Ullmanns Enc., vol. A 12, Fifth Edt. pp. 16–24.

* cited by examiner

Primary Examiner—Alan L. Rotman
Assistant Examiner—Héctor Reyes
(74) Attorney, Agent, or Firm—Keil & Weinkauf

(57) ABSTRACT

The invention relates to a process for the preparation of anhydrous or substantially anhydrous formic acid. The process has the special feature that a liquid of the general formula I

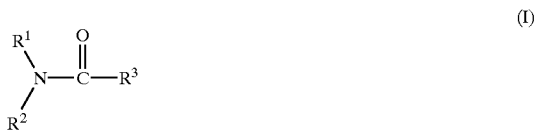

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group, employed as extractant is also employed as washing liquid for the offgases produced in the process.

8 Claims, 4 Drawing Sheets

METHOD FOR CLEANING OFF-GAS FLOWS

Figure 1:
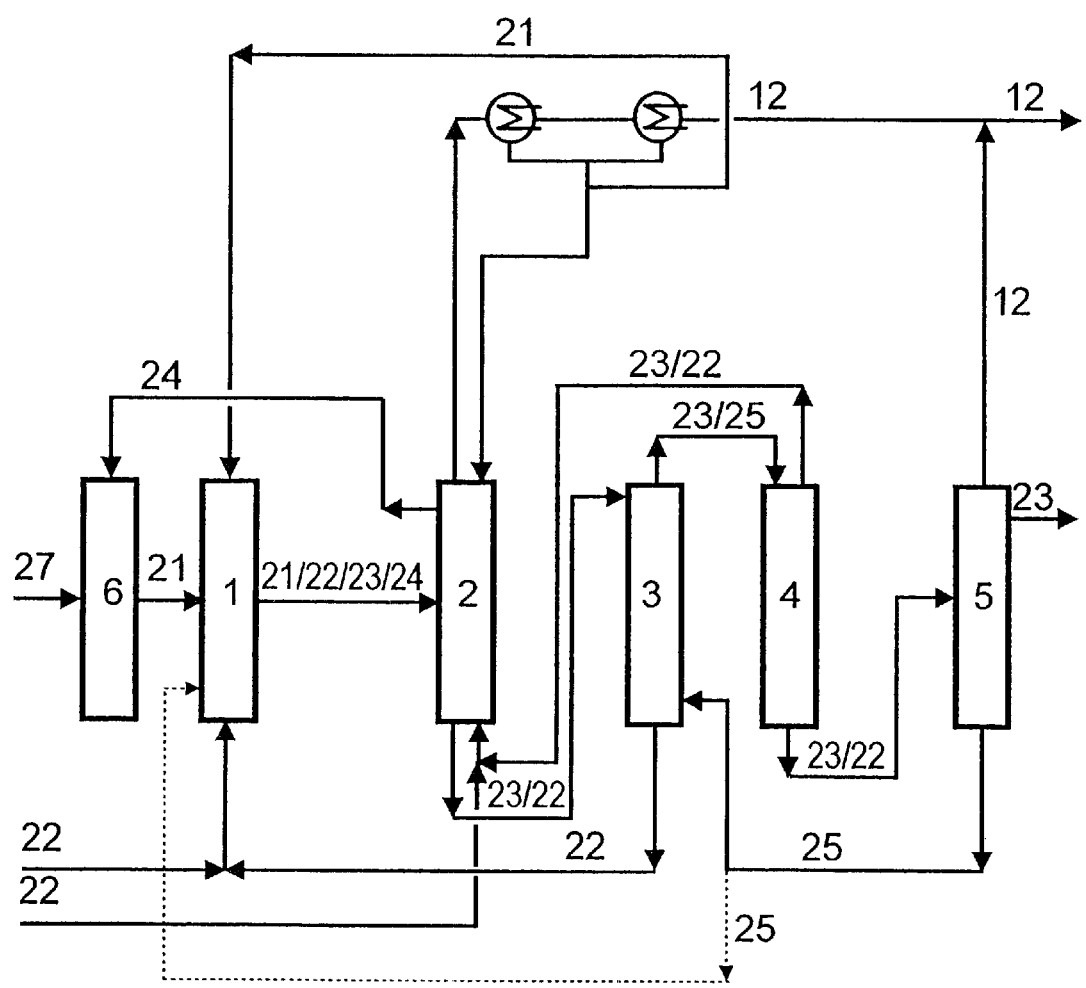

The present invention relates to an apparatus and a process for obtaining anhydrous or substantially anhydrous formic acid, and to the use of the extractant employed in the process.

"Ullmanns Encyklopädie der technischen Chemie" [Ullmann's Encyclopedia of Industrial Chemistry], 4$^{th}$ Edition, Volume 7, page 365, discloses that formic acid can be prepared by acidolysis of formamide using sulfuric acid. However, this process has the disadvantage that stoichiometric amounts of ammonium sulfate are obtained as an unavoidable product.

Another way of preparing formic acid consists in the hydrolysis of methyl formate, which is synthesized from methanol and carbon monoxide. This synthesis is based on the following equations:

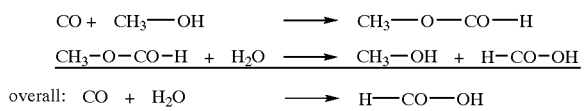

The hydrolysis of methyl formate described in "Ullmanns Encyklopädie der technischen Chemie" [Ullmann's Encyclopedia of Industrial Chemistry], 4$^{th}$ Edition, Volume 7, page 366

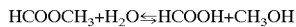

has the disadvantage of an unfavorable position of the hydrolysis equilibrium. A shift in the equilibrium by removing the desired process products by distillation is not possible since methyl formate (boiling point 32° C.) boils significantly lower than methanol (boiling point 65° C.) and formic acid (boiling point 101° C.). Anhydrous formic acid cannot easily be obtained from the resultant aqueous formic acid solution by distillation since it forms an azeotrope with water. The difficulty thus consists in obtaining anhydrous formic acid from the methyl formate hydrolysis mixture.

A process described in EP-B-0 017 866 which comprises steps a) to g) enables the preparation of anhydrous formic acid starting from methyl formate. Anhydrous formic acid is obtained here if a) methyl formate is subjected to hydrolysis,
b) methanol and excess methyl formate are distilled off from the resultant hydrolysis mixture,
c) the bottom product from the distillation (b), which comprises formic acid and water, is extracted in a liquid-liquid extraction with an extractant which principally takes up the formic acid,
d) the resultant extract phase, comprising formic acid, extractant and some of the water, is subjected to distillation,
e) the top product obtained in this distillation, which comprises water and some of the formic acid, is fed back into the lower part of the distillation column in step (b),
f) the bottom product from distillation step (d), which predominantly comprises extractant and formic acid, is separated into anhydrous formic acid and the extractant by distillation, and
g) the extractant leaving step (f) is fed back into the process.

In this process, it is particularly advantageous h) to carry out distillation steps (b) and (d) in a single column,
i) to introduce the water necessary for the hydrolysis in the form of steam into the lower part of the column provided for carrying out step (b),
k) to employ methyl formate and water in the hydrolysis (a) in a molar ratio of from 1:2 to 1:10, and/or
l) to employ, as extractant, a carboxamide of the general formula I

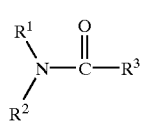

(I)

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group.

Steps (a) to (i) of the above-described process disclosed in EP-B-0 017 866 are explained in greater detail below.

Step (a)

The hydrolysis is usually carried out at a temperature in the range from 80 to 150° C.

Step (b)

The distillation of the hydrolysis mixture can in principle be carried out at any desired pressure, preferably from 0.5 to 2 bar. In general, working under atmospheric pressure is advisable. In this case, the temperature at the bottom of the column is about 110° C. and the temperature at the top of the column is from about 30 to 40° C. The hydrolysis mixture is advantageously added at a temperature in the range from 80 to 150° C., and the methanol is preferably removed in liquid form at a temperature of from 55 to 65° C. Satisfactory separation of the mixture into methyl formate and methanol on the one hand and aqueous formic acid on the other hand is possible even using a distillation column which has 25 theoretical plates (the theoretical number of plates is preferably from 35 to 45). Any design can be used for the column intended for step (b), but a sieve-plate or packed column is particularly recommended.

Step (c)

The liquid-liquid extraction of the formic acid from its aqueous solution by means of an extractant is preferably carried out at atmospheric pressure and a temperature of from 60 to 120° C., in particular from 70 to 90° C., in countercurrent. Depending on the type of extractant, extraction devices having from 1 to 12 theoretical separation stages are generally required. Suitable extraction devices for this purpose are in particular liquid-liquid extraction columns. In most cases, satisfactory results are achieved using from 4 to 6 theoretical separation stages.

The choice of extractant is not limited. Particularly suitable extractants are carboxamides of the general formula I given above. Extractants of this type are, in particular, N-di-n-butylformamide and in addition N-di-n-butylacetamide, N-methyl-N-2-heptylformamide, N-n-butyl-N-2-ethylhexylformamide, N-n-butyl-N-cyclohexylformamide and N-ethylformanilide, and mixtures of these compounds. Further suitable extractants are, inter alia, diisopropyl ether, methyl isobutyl ketone, ethyl acetate, tributyl phosphate and butanediol formate.

Step (d)

The extract phase is separated by distillation in an appropriate distillation device into a liquid phase, which generally comprises predominantly formic acid and extractant, and a vapor phase predominantly comprising water and small amounts of formic acid. This is an extractive distillation. The bottom temperature is preferably from 140 to 180° C. A satisfactory separation effect is generally achieved from 5 theoretical plates.

Step (e)

The formic acid/water mixture is generally recycled in vapor form.

Steps (f) and (g)

The distillation device (usually in the form of a column) for carrying out step (f) is advantageously operated under reduced pressure—from about 50 to 300 mbar and correspondingly low head temperatures—from about 30 to 60° C.

Step (h)

This variant of the process relates to steps (b) and (d). The distillation devices for carrying out steps (b) and (d) are arranged in an overall distillation device. The distillation devices here are generally in the form of columns.

Step (i)

In this step, water required for the hydrolysis is provided in the form of steam.

In the process, offgas streams are liberated, in particular at the tops of the distillation columns present. These streams are generally passed through condensers, where condensable components are condensed out and then fed back into the process. The components which have not condensed out in the condensers and remain in the gas phase are discarded as offgas or fed to offgas combustion. Offgas combustion is expensive. In addition, valuable products, in particular methyl formate, methanol and/or formic acid, are generally present in the offgas stream. Combustion of these valuable materials reduces the economic efficiency of the process. However, the discharge of offgas streams, which, in addition to the abovementioned valuable products, generally also contain inert gases, for example carbon monoxide, is necessary since otherwise inert gases would accumulate in the process, and the function of the condensers would be impossible.

It is an object of the present invention to provide a process in which offgas streams are discharged from the process, but the losses of valuable products and disposal costs are minimized. It is essential that the process is economical to carry out.

We have found that this object is achieved by a process for obtaining anhydrous or substantially anhydrous formic acid in which i) methyl formate is subjected to hydrolysis, ii) methanol and excess methyl formate are distilled off from the resultant hydrolysis mixture, iii) the bottom product from distillation ii), comprising formic acid and water, is extracted in a liquid-liquid extraction with an extractant which principally takes up the formic acid, and the extractant employed here is a carboxamide of the general formula I

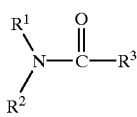

(I)

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group, iv) the resultant extract phase, comprising formic acid, extractant and some of the water, is subjected to distillation, v) the top product obtained in this distillation, which comprises water and some of the formic acid, is fed back into the lower part of the distillation device in step ii), vi) the bottom product from distillation step iv), which comprises predominantly extractant and formic acid, is separated by distillation into anhydrous or substantially anhydrous formic acid and the extractant, and vii) the extractant leaving step vi) is fed back into the process, which comprises washing gaseous offgas streams arising in the process and comprising methyl formate and/or methanol and/or formic acid with the extractant employed before discharge from the process, during which methyl formate and/or methanol and/or formic acid dissolve in the extractant, and the extractant loaded with methyl formate and/or methanol and/or formic acid is fed back into the process.

One or more offgas streams can be washed with the extractant in the process. It is advantageous for offgas streams to be combined and subsequently subjected to the washing. However, it is also possible for a plurality of offgas streams to be introduced into the offgas washing device provided for the offgas washing.

The offgas streams washed with extractant can advantageously be disposed of without subsequent offgas combustion. This saves considerable costs. Recycling of the valuable products, in particular methyl formate and/or methanol and/or formic acid, also enables considerable costs to be saved. It is essential that the solvent employed for the washing is simultaneously employed as extractant for the formic acid and as washing liquid for the offgas—for carrying out the offgas washing, there is therefore no need to introduce a further additional assistant into the process. This is of considerable economic importance.

The extractants employed for the process are of relatively low volatility and therefore cannot be stripped out of the offgas stream to be cleaned.

Preferred extractants are N,N-di-n-butylformamide, N,N-di-n-butylacetamide, N-methyl-N-2-heptylformamide, N-n-butyl-N-2-ethylhexylformamide, N-n-butyl-N-cyclohexylformamide and/or N-ethylformanilide. It is possible both to employ only one extractant and to employ a mixture of a plurality of extractants. The extractant employed for the washing may, in addition to the "actual extractant", also comprise other components, in particular formic acid. The extractant is usually fed to the offgas washing device at a temperature of from 10 to 60° C., in particular from 20 to 50° C.

In general, the offgas streams washed with the extractant employed arise in step ii) and/or step vi) of the process according to the invention. The offgas streams are generally removed from the top of the corresponding distillation columns and fed to condensers. Before the washing, condensable components present in the offgas stream are then correspondingly partially removed from the offgas streams by condensation. The components condensed out are then generally fed back into the process while the offgas freed from the components condensed out is fed to the washing. In this connection, the term "condensable components" is taken to mean components such as methanol, formic acid or methyl formate which can be condensed out at 0° C. and atmospheric pressure—inert gases, such as nitrogen or carbon monoxide, should be regarded as non-condensable components, since these remain in the offgas stream in their entirety. By contrast, condensable components are generally only partially condensed. The uncondensed components enter the offgas stream which is washed with the extractant.

The extractant loaded with methyl formate and/or methanol and/or formic acid after washing is usually fed back into the process in step iii) and/or step iv)—this generally corresponds to the recycling into the extractant device and/or into the distillation device for carrying out step vi).

In general, the extractant employed for the washing is taken as a sub-stream from the extractant leaving step vi) and/or the extract phase leaving step iii), which essentially comprises formic acid and extractant.

The washing of the offgas with the extractant is generally carried out in an offgas washing device.

The invention also relates to the use of a carboxamide of the general formula I

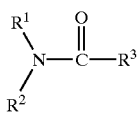
(I)

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group, in the above-described process as extractant for the liquid-liquid extraction of formic acid and as washing liquid for gaseous offgas streams comprising methyl formate and/or methanol and/or formic acid.

An apparatus for carrying out the process explained above is also provided in accordance with the invention. This comprises α) a synthesis reactor,
β) a hydrolysis reactor,
χ) a distillation device for carrying out step ii),
δ) a distillation device for carrying out step iv),
ε) an extraction device,
φ) a distillation device for carrying out step vi), and
γ) an offgas washing device.

The term "synthesis reactor" is taken to mean a device in which firstly the synthesis of methyl formate is carried out (usually in a corresponding reactor) and in which secondly, if desired, separation of the synthesis mixture obtained is carried out (usually in a distillation device downstream of the reactor). The hydrolysis reactor employed can be any desired reactor with which the hydrolysis of methyl formate can be carried out. Suitable distillation devices are, in particular, distillation columns. For the extractant of formic acid, use is made, in particular, of an extractant device in the form of a liquid-liquid extractant column. For carrying out the offgas washing, use is generally made of an offgas washing device, which is preferably in the form of a washing column. This usually has from 3 to 20, in particular from 4 to 10, theoretical separation stages.

In a preferred embodiment of the invention, the distillation device for carrying out step ii) and the distillation device for carrying out step iv) are arranged in a single distillation device. The latter is generally in the form of a distillation column.

Figure 2:
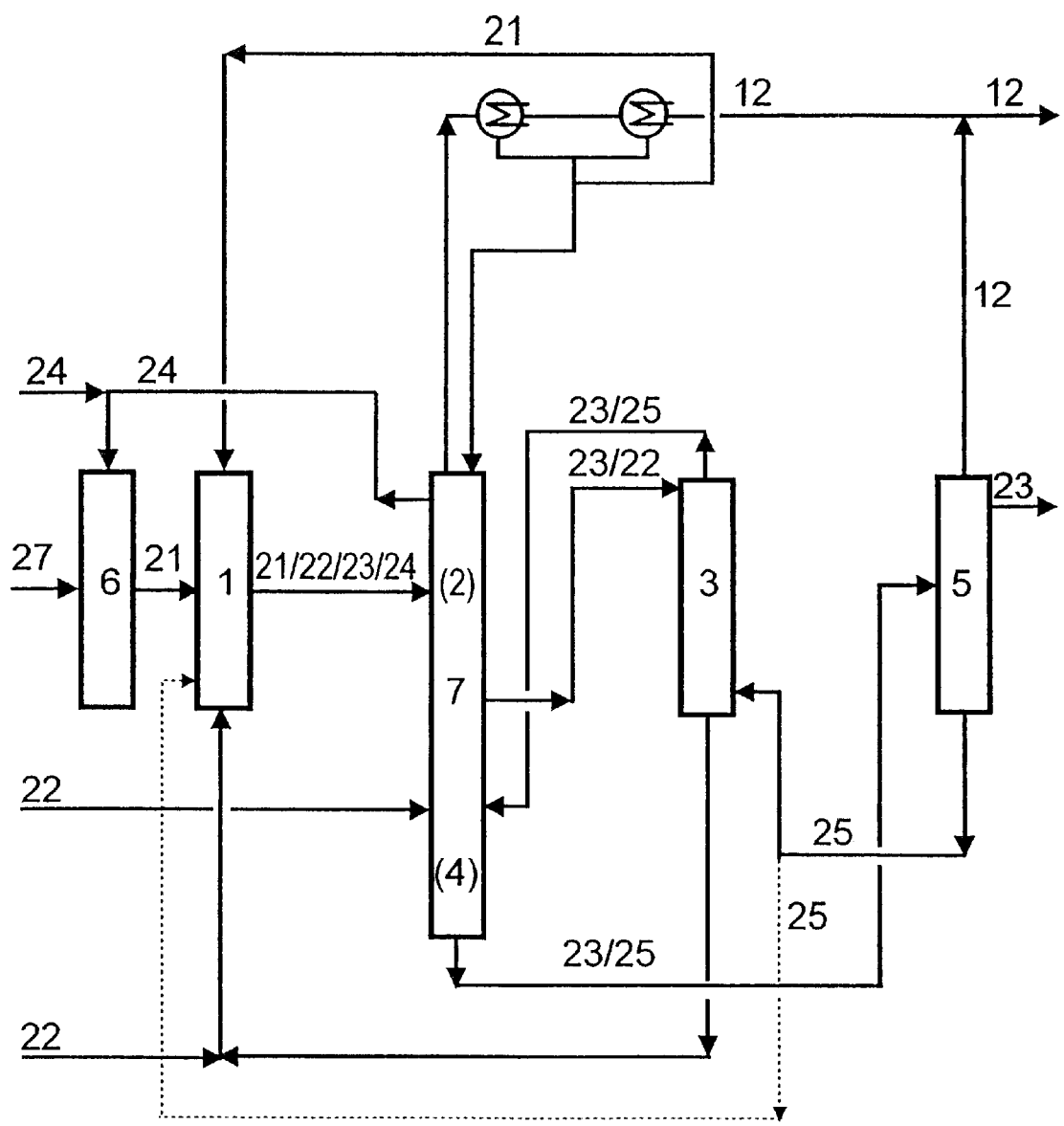
Figure 3:
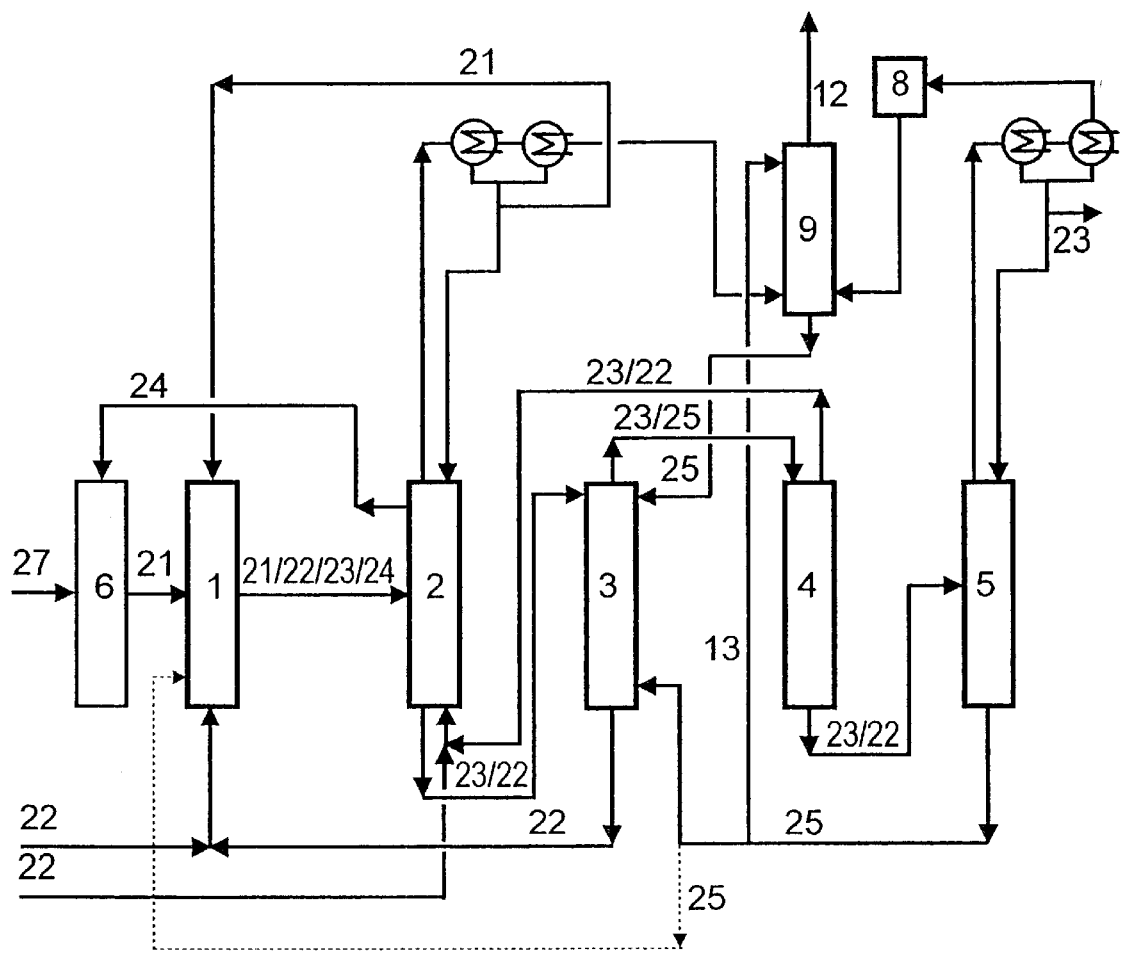
Figure 4:
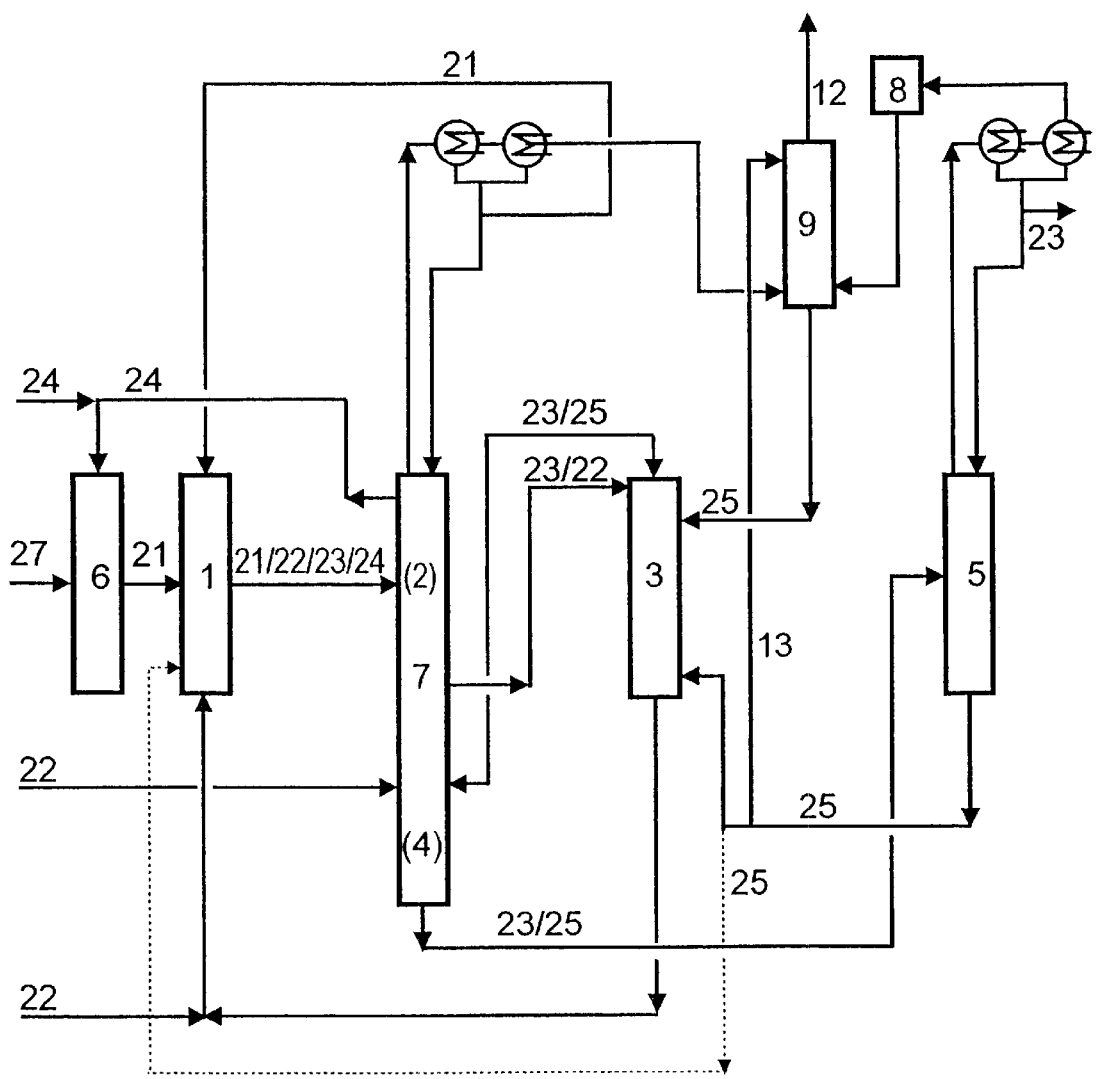

The attached drawing shows in FIG. 1 and in FIG. 2 diagrams of plants for carrying out the prior art process, and in FIG. 3 and in FIG. 4 diagrams of plants for carrying out the process according to the invention.

The streams denoted by arrows are in some cases provided with reference numerals. These indicate the components present in these streams, generally with the greatest proportion therein. Since the proportions of the components in the streams can vary, these reference numerals only serve as guide values. 21 here denotes methyl formate, 22 denotes water, 23 denotes formic acid, 24 denotes methanol, 25 denotes extractant and 27 denotes carbon monoxide. It is common to the plants for carrying out the prior art process (FIG. 1, FIG. 2) and the plants for carrying out the process according to the invention (FIG. 3, FIG. 4) that they comprise a synthesis reactor 6, a hydrolysis reactor 1, a distillation device 2 for carrying out step ii), a distillation device 4 for carrying out step iv), an extraction device 3 for carrying out step iii) and a distillation device 5 for carrying out step vi). The distillation devices 2; 4 here may be arranged in a single distillation device 7.

In contrast to the plants shown in FIG. 1 and FIG. 2, the plants for carrying out the process according to the invention shown in FIG. 3 and FIG. 4 have a vacuum pump 8, a gas-washing device 9 and a line 13 for feeding extractant into the gas-washing device 9. In the prior art plants (FIG. 1, FIG. 2), the offgas leaves the process via line 12, which is arranged downstream of condensers. In the plants according to the invention (FIG. 3, FIG. 4), by contrast, line 12, through which the offgas is discharged from the process, is downstream of the offgas washing device 9.

The invention will be explained in greater detail below with reference to a working example.

EXAMPLE

The example is based on a process according to the invention carried out in a plant shown diagrammatically in FIG. 4. 5.3 kg/h of aqueous formic acid are prepared continuously in the plant. 94.7 l/h of offgas are produced, which are freed from condensable components (formic acid, methyl formate and methanol) in an offgas washing device 9 using 1.1 kg/h of the extractant N,N-di-n-butylformamide. The laboratory column employed as offgas washing device has a diameter of 30 mm and is fitted with 30 bubble-cap plates.

The results of the experiment are shown in Table 1 below.

TABLE 1

|  | Formic acid | Offgas (uncleaned) | Offgas (cleaned) | Extractant (unloaded) | Extractant (loaded) |
|---|---|---|---|---|---|
| Amount produced per time unit, kg/h | 5.300 | 0.176 | 0.082 | 1.113 | 1.207 |
| Water Composition, % by wt. | 5.7 | 0 | 0 | 0 | 0 |

TABLE 1-continued

| | Formic acid | Offgas (uncleaned) | Offgas (cleaned) | Extractant (unloaded) | Extractant (loaded) |
|---|---|---|---|---|---|
| Extractant Composition, % by wt. | 0 | 0 | 0 | 99.1 | 91.4 |
| Formic acid Composition, % by wt. | 94.3 | 3.9 | 0 | 0.9 | 1.4 |
| Methyl formate Composition, % by wt. | 0 | 49.4 | 1.8 | — | 7.1 |
| Methanol Composition, % by wt. | 0 | 1.1 | 0 | — | 0.2 |
| Inert gas Composition, % by wt. | 0 | 45.6 | 98.2 | — | 0 |
| Temperature, °C. | — | 47 | 31 | 30 | 46 |

The experimental results show that the offgas after washing has been substantially freed from the valuable products formic acid, methyl formate and methanol. The cleaned offgas now contains only 1.8% by weight of valuable products, while the uncleaned offgas contains a total of 54.4% by weight of valuable products. It is found that the extractant N,N-di-n-butylformamide employed is suitable as washing liquid for the offgases liberated in the process.

We claim:

1. A process for obtaining anhydrous or substantially anhydrous formic acid, in which
   i) methyl formate is subjected to hydrolysis,
   ii) methanol and excess methyl formate are distilled off from the resultant hydrolysis mixture,
   iii) the bottom product from distillation ii), comprising formic acid and water, is extracted in a liquid-liquid extraction with an extractant which principally takes up the formic acid, and the extractant employed here is a carboxamide of the general formula I

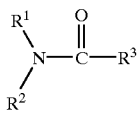

(I)

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group,
   iv) the resultant extract phase, comprising formic acid, extractant and some water, is subjected to distillation,
   v) the top product obtained in this distillation, which comprises water and some of the formic acid, is fed back into the lower part of the distillation device in step ii),
   vi) the bottom product from distillation step iv), which comprises predominantly extractant and formic acid, is separated by distillation into anhydrous or substantially anhydrous formic acid and the extractant, and
   vii) the extractant leaving step vi) is fed back into the process, which comprises washing gaseous offgas streams arising in the process and comprising methyl formate or methanol or formic acid or a mixture thereof with the extractant employed before discharge from the process, during which methyl formate or methanol or formic acid or a mixture thereof dissolve in the extractant, and the extractant loaded with methyl formate or methanol or formic acid or a mixture thereof is fed back into the process.

2. The process as claimed in claim 1, wherein the extractant employed is selected from the group consisting of N,N-di-n-butylformamide, N,N-di-n-butylacetamide, N-methyl-N-2-heptylformamide, N-n-butyl-N-2-ethylhexylformamide, N-n-butyl-N-cyclohexylformamide and N-ethylformanilide.

3. The process as claimed in claim 1, wherein the extractant loaded with methyl formate or methanol or formic acid or a mixture thereof is fed back into the process in step iii) or step iv) or both steps.

4. The process as claimed in claim 1, wherein the offgas streams washed with the extractant employed are produced in at least one of steps ii) and vi), and condensable components are removed from the offgas streams by condensation before the washing.

5. The process as claimed in claim 1, wherein the extractant employed for the washing is taken as a sub-stream from the extractant leaving step vi) or from the extract phase leaving step iii), which essentially comprises formic acid and extractant, or from both.

6. The process as claimed in claim 1, wherein distillation steps ii) and iv) are carried out in a single distillation device.

7. An apparatus for carrying out a process as claimed in claim 1, comprising
   α) a synthesis reactor (6),
   β) a hydrolysis reactor (1),
   χ) a distillation device (2) for carrying out step ii),
   δ) a distillation device (4) for carrying out step iv),
   ε) an extraction device (3),
   φ) a distillation device (5) for carrying out step vi), and
   γ) an offgas washing device (9).

8. An apparatus as claimed in claim 7, wherein the distillation device (2) for carrying out step ii) and the distillation device (4) for carrying out step iv) are arranged in a single distillation device (7).

* * * * *